(12) United States Patent
Shibata et al.

(10) Patent No.: US 8,203,706 B2
(45) Date of Patent: Jun. 19, 2012

(54) METHOD AND APPARATUS FOR INSPECTING DEFECTS

(75) Inventors: Yukihiro Shibata, Fujisawa (JP); Yasuhiro Yoshitake, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 450 days.

(21) Appl. No.: 12/423,902

(22) Filed: Apr. 15, 2009

(65) Prior Publication Data
US 2009/0279079 A1    Nov. 12, 2009

(30) Foreign Application Priority Data
Apr. 16, 2008    (JP) .................................. 2008-106579

(51) Int. Cl.
*G01N 21/00*    (2006.01)
(52) U.S. Cl. .................................. 356/237.2; 356/237.3
(58) Field of Classification Search .... 356/237.1–237.5, 356/394, 445–448
See application file for complete search history.

(56) References Cited

U.S. PATENT DOCUMENTS

| | | | |
|---|---|---|---|
| 6,084,664 A * | 7/2000 | Matsumoto et al. | 356/237.4 |
| 7,859,656 B2 * | 12/2010 | Uto et al. | 356/237.2 |
| 2003/0081201 A1 * | 5/2003 | Shibata et al. | 356/237.2 |
| 2006/0012781 A1 * | 1/2006 | Fradkin et al. | 356/237.5 |
| 2007/0031108 A1 * | 2/2007 | Sugita et al. | 385/147 |
| 2007/0081151 A1 * | 4/2007 | Shortt et al. | 356/237.2 |

FOREIGN PATENT DOCUMENTS

| | | |
|---|---|---|
| JP | 5-142156 | 6/1993 |
| JP | 6-167458 | 6/1994 |
| JP | 2004-184142 | 7/2004 |
| JP | 2005-521899 | 7/2005 |
| JP | 2007-147475 | 6/2007 |
| WO | WO 03/083560 A2 | 10/2003 |

* cited by examiner

*Primary Examiner* — Hoa Pham
(74) *Attorney, Agent, or Firm* — Antonelli, Terry, Stout & Kraus, LLP.

(57) ABSTRACT

To provide a defect inspection apparatus for inspecting defects of a specimen without lowering resolution of a lens, without depending on a polarization characteristic of a defect scattered light, and with high detection sensitivity that is realized by the following. A detection optical path is branched by at least one of spectral splitting and polarization splitting, a spatial filter in the form of a two-dimensional array is disposed after the branch, and only diffracted light is shielded by the spatial filter in the form of a two-dimensional array.

12 Claims, 15 Drawing Sheets

FIG.3A   FIG.3B
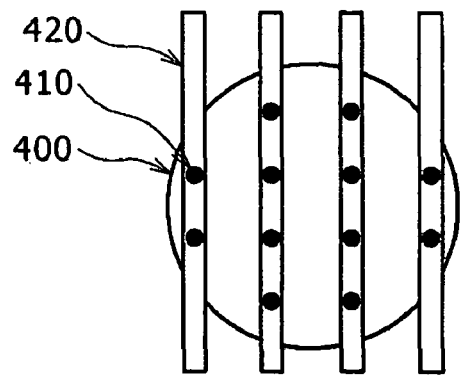
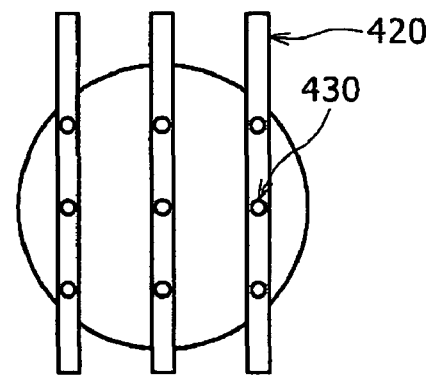
FIG.3C
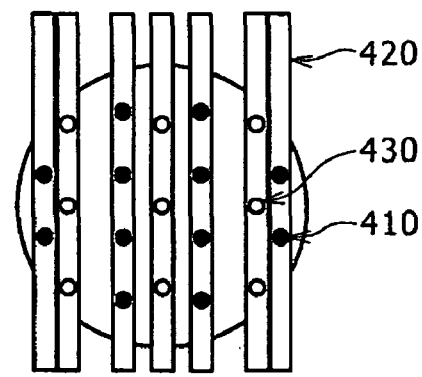
FIG.3D
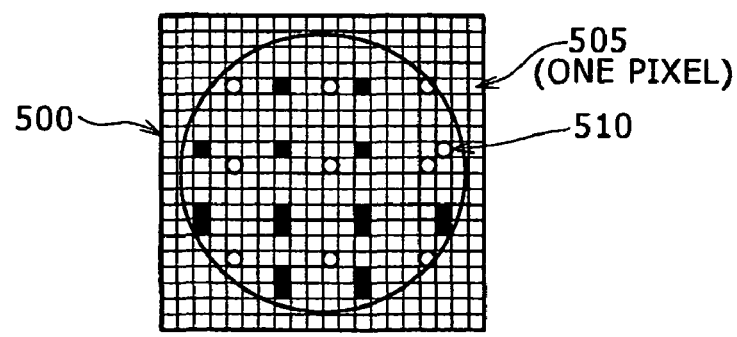

ANALYZER
TRANSMISSION
AXIS

METHOD AND APPARATUS FOR INSPECTING DEFECTS

BACKGROUND OF THE INVENTION

The present invention relates to a defect inspection method and a defect inspection apparatus that uses this, and more specifically, to a defect inspection method for detecting defects of a minute pattern formed on a substrate through a film process that is typified by a semiconductor manufacture process and a manufacture process of flat panel display, foreign materials, etc. and a defect inspection apparatus that uses this.

As a conventional apparatus for detecting defects of a specimen, there is a patent of International Publication WO 2003/083560. This inspection apparatus is equipped with a dark field detecting optical system that detects scattered light on a wafer by illuminating the wafer surface slantingly with a light of a single wavelength. Diffracted light from a periodic pattern coming into this optical system is shielded by a spatial filter disposed at a rear side focal point position (an exit pupil position). As this spatial filter, a configuration that uses a liquid crystal filter conformed to ultraviolet rays is shown.

Various patterns are formed on the semiconductor wafer and kinds of defects have also great varieties according to generation causes. In the optical dark-field detection system, a laser is used as a light source, which provides an illumination light of a single wavelength.

However, with the light of the single wavelength, there is the case where the scattered light can hardly be obtained from the defect depending on optical constants of a defective material and the shape and structure around the defect. As one example, although a silicon oxide film is used as an electric insulation film of the patterns that are stacked, an optically transparent oxide film generates thin film interference; therefore the intensity of the scattered light will vary depending on its film thickness. Because of this phenomenon, the scattered light becomes extremely small with a film thickness condition of weakening light rays and becomes undetectable. As a countermeasure against this, the number of illumination wavelengths is increased to a plural number. By this modification, even under a film thickness condition under which the amount of detected light is insufficient with a single wavelength, a probability of being able to secure the amount of light necessary for defect detection at the other wavelength(s) is increased.

In this way, although it is possible to improve a capture ratio of defects with illumination of a plurality of wavelengths, the diffracted light from the periodic pattern, such as the memory cell part, has a different position of a diffracted image for each wavelength because a diffraction angle is expressed by a function of wavelength. FIG. 3 shows a schematic diagram of the diffracted image when the periodic pattern is illuminated by the illumination lights of wavelengths $\lambda_1$, $\lambda_2$ ($\lambda_1$ is a relatively short wavelength) (hereinafter referred to as a $\lambda_1$ light and a $\lambda_2$ light). This diagram is a schematic diagram of the diffracted image formed at an exit pupil 400 of an objective lens. FIG. 3A shows a diffracted image (diffracted light) 410 of the $\lambda_1$ light, and FIG. 3B shows a diffracted image (diffracted light) 430 of the $\lambda_2$ light. The diffracted image 410 occurs in a direction of periodicity of the pattern. An example of FIGS. 3A, 3B, and 3C is an example of the diffracted image of a pattern that is formed periodically in two directions intersecting at right angles.

As means for shielding these diffracted images, there is a technique of shielding the image by fitting a light shielding belt 420 to a pitch of the diffracted image. When lights of two wavelengths $\lambda_1$, $\lambda_2$, are simultaneously cast for illumination, regarding the diffracted images actually detected, the two diffracted images of wavelength $\lambda_1$, $\lambda_2$, are detected at the exit pupil 400 of the objective lens. Because of this, the number of the diffracted images becomes large as shown in FIG. 3C. If these images are intended to be shielded, the number of the light shielding belts will become large and an aperture ratio of the exit pupil will lower. Since this leads to lowering of substantial resolution, there is a problem to be solved that contrast of a minute defect decreases and defect detection sensitivity lowers.

In addition, when the liquid crystal filter is used as the spatial filter, it is necessary that the scattered light is filtered so as to become a linearly polarized light and alignment of the liquid crystal is electrically controlled to make it perform optical rotation. It becomes possible to control the transmittance of the light that is transmitted through a polarizing plate disposed on an image plane side depending on the amount of this optical rotation.

However, the polarization state of the scattered light changes according to a shape, a structure, a material, etc. of the pattern and the defect. Therefore, if the scattered is filtered so as to become a linearly polarized light one the object side (wafer side) of the liquid crystal, in the case where the defect scattered light is polarized in a direction perpendicular to a filter transmission axis, the scattered light of the defect will be shielded and accordingly it will become impossible to detect the defect.

SUMMARY OF THE INVENTION

Provided is a method for detecting the defects of a specimen with a circuit pattern formed on it, where lights of a plurality of wavelengths are illuminated onto the specimen slantingly, scattered and diffracted light from the pattern and the defect are captured by an objective lens, the diffracted light for a periodic pattern is shielded by a spatial filtering device in the form of an array, light that was not shielded is subjected to branching by at least one or more of spectral splitting and polarization splitting, and images are detected on image planes of the respective optical paths that were branched in the above and are processed to determine a defect candidate.

Moreover, the spatial filtering device is a group of optical shutters each using a liquid crystal or double refection element or of optical shutters each using MEMS, and has a structure in which the optical shutters are arranged in the form of a two-dimensional array and that can electrically control transmitted light of the device.

It is characterized by using a reflection type DMD as the spatial filtering device and utilizing polarization for branching the incident light to the DMD and the reflected light after the filtering.

Moreover, it is characterized by that the spatial filtering device is a liquid crystal tunable filter in which Lyot filters are arranged one-dimensionally or two-dimensionally.

Moreover, it is characterized by that a light source for illuminating a specimen is a lamp, or a plurality of lasers, or a laser that emits laser beams of a plurality of wavelengths.

Moreover, it ids characterized by that defect determination is performed using plural kinds of images that differ from one another in at least one condition of the wavelength condition and the polarization condition; when the defect candidate is determined by comparison processing of the plural kinds, a determination result and the image that was subjected to determination processing are stored; and regarding the image that was not determined as a defect, then image in the identical space as in the defect candidate is stored, a feature quantity of the image in the identical space but under a different condition is computed, and the defect determination or sorting is performed again.

According to the present invention, it is possible to improve a capture ratio of defects by stably detecting scattered light to be detected that varies according to a shape, a structure, and a material of the defect with an illumination of a plurality of wavelengths.

Moreover, also in the case of the illumination with lights of a plurality of wavelengths, inspection sensitivity is improved by shielding the diffracted light of a normal pattern while suppressing lowering of an aperture ratio of a detection optical system and thereby detecting the scattered light of minute defects efficiently.

Further, in the case where the polarization state of scattered light differs from others depending on a defect kind, it is possible to improve the capture ratio of defects by performing spatial filtering without shielding the scattered light of the defect.

These and other objects, features and advantages of the invention will be apparent from the following more particular description of preferred embodiments of the invention, as illustrated in the accompanying drawings.

BRIEF DESCRIPTION OF THE DRAWINGS

FIG. 3A is a schematic diagram of a diffracted image formed at an exit pupil of an objective lens when a periodic pattern is illuminated by an illumination light of a wavelength $\lambda_1$;

FIG. 3B is a schematic diagram of a diffracted image formed at the exit pupil of the objective lens when the periodic pattern is illuminated by an illumination light of a wavelength $\lambda_2$ and an explanatory diagram of the diffracted image and spatial filtering at the exit pupil position;

FIG. 3C is the diffracted image that is detected at the exit pupil of the objective lens when the periodic pattern is illuminated simultaneously by the illumination light of a wavelength $\lambda_1$ and the illumination light of a wavelength $\lambda_2$;

FIG. 3D is a diagram showing one example of a spatial filter whose filtering pattern can be changed to a suitable one during inspection according to the pitch and shape of a pattern on a wafer;

DESCRIPTION OF THE PREFERRED EMBODIMENTS

Hereafter, embodiments will be described in detail using drawings.

First Embodiment

Figure 1:
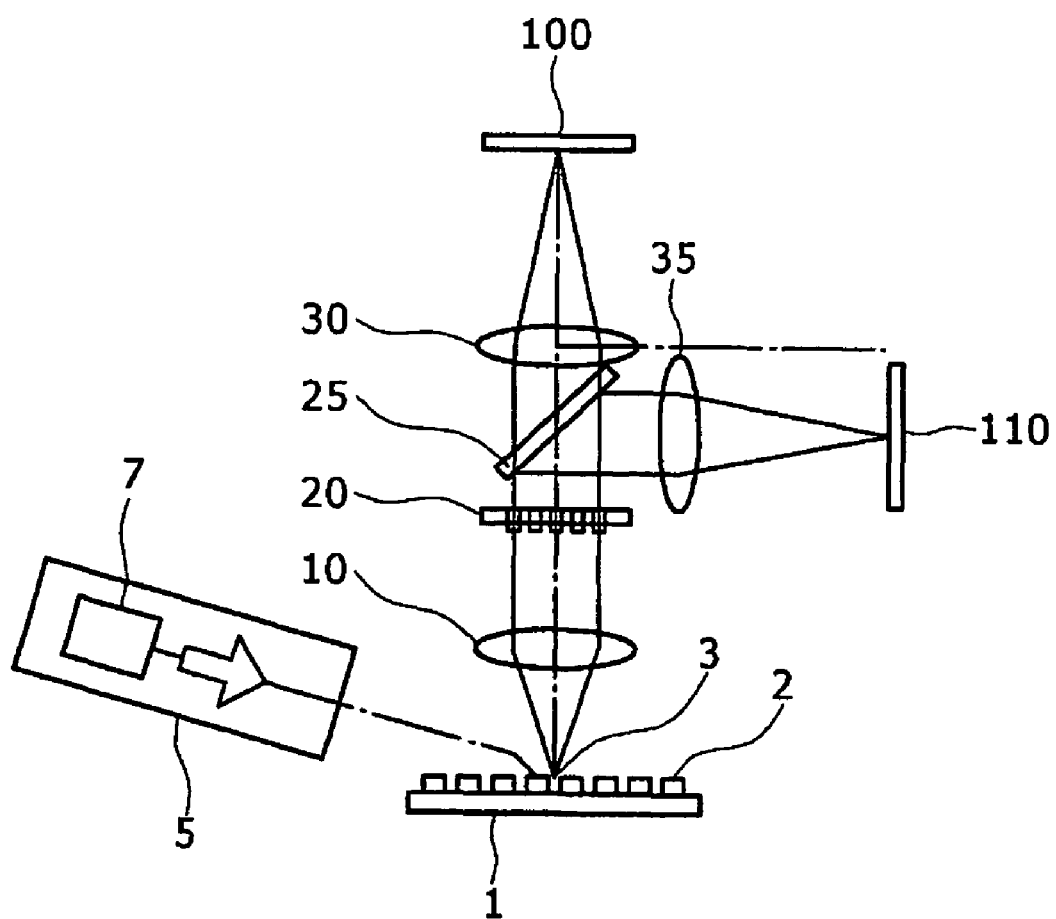
FIG. 1 is a diagram showing an outline configuration of an optical system shown in this first embodiment.

FIG. 1 shows a configuration of an apparatus for detecting defects of a specimen according to the present invention. A pattern 2 is formed on a wafer 1 and a defect 3 exists on the pattern 2. The wafer 1 is illuminated by an illumination optical system 5 of a plurality of wavelengths (in this embodiment, two wavelengths $\lambda_1$, $\lambda_2$) that is disposed slantingly relative to the wafer 1. For a light source 7 used in an illumination optical system 5, lights ranging from DUV (Deep Ultraviolet) lights to the visible lights such as: mercury lamps emitting the d line (588 nm), the e line (546 nm), the g line (436 nm), the h line (405 nm), and the i line (365 nm); a second harmonic 532 nm laser of YAG; a third harmonic (355 nm) or fourth harmonic (266 nm) laser; and a 199 nm laser. Among them, lights of two wavelengths ($\lambda_1, \lambda_2$) are cast on the wafer 1 for illumination from the illumination optical system. Among pieces of light scattered by the pattern 2 and the defect 3, light that propagates to an objective lens 10 within its NA (Numerical Aperture) is captured by the objective lens 10 and forms a diffracted image at a rear side focal (an exit pupil) position of the objective lens 10. A spatial filter 20 is disposed at this rear side focal point position or its conjugate position, and diffracted light from the periodic normal pattern 2 is shield. The light that is transmitted through the spatial filter 20 is branched to optical paths by a dichroic mirror 25 depending on its wavelength. The light of a wavelength $\lambda_1$ (hereinafter referred to as the $\lambda_1$ light) that was transmitted through the dichroic mirror 25 forms an image of the wafer 1 on an image sensor 100 through an image formation lens 30. On the other hand, the light of a wavelength 2 (hereinafter referred to as the $\lambda_2$ light) that reflected dichroic mirror 25 forms a scattered image on an image sensor 110 though an image formation lens 35.

Figure 2:
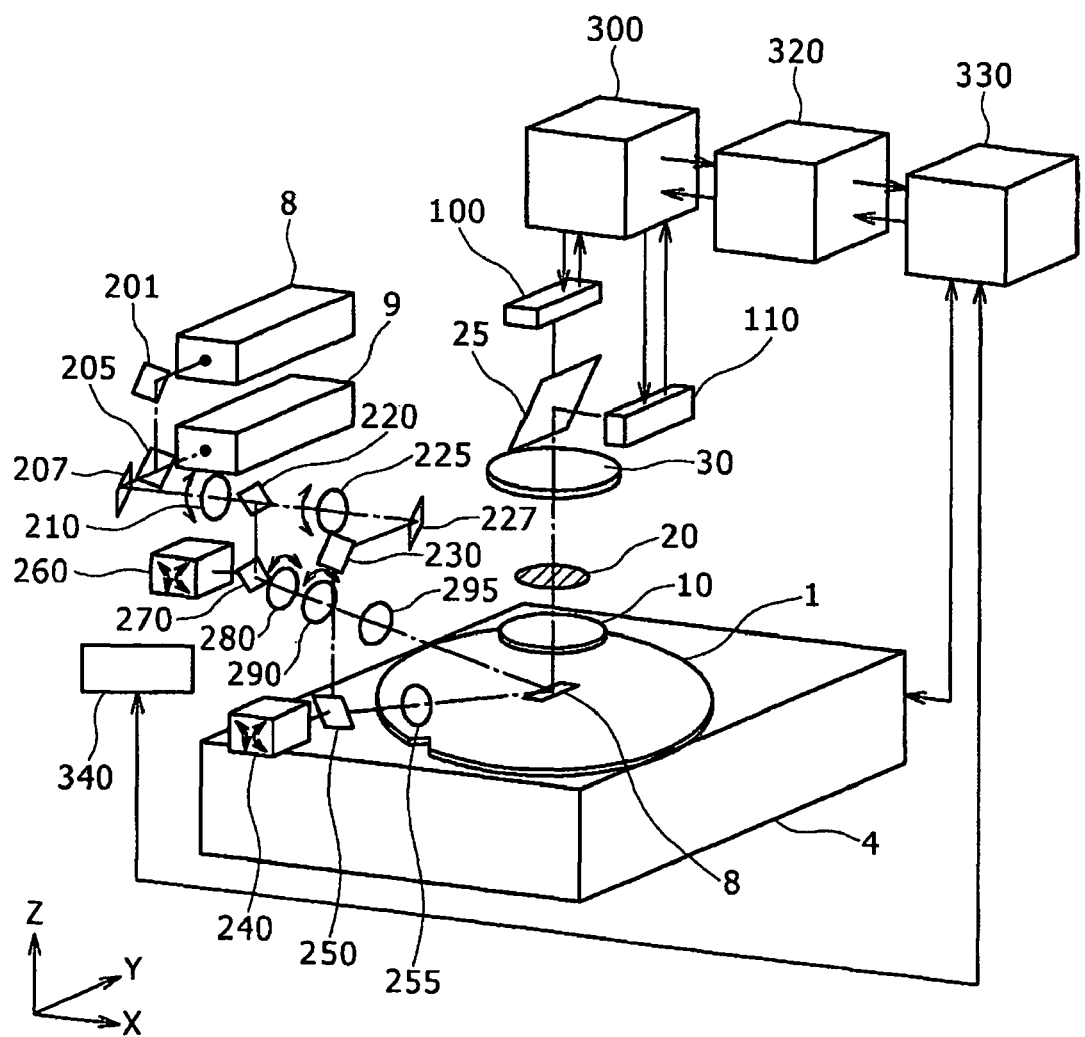
FIG. 2 is a diagram showing an outline configuration of an inspection apparatus shown in this first embodiment.

FIG. 2 shows a configuration of an inspection apparatus using this optical system. The wafer 1 is mounted on a stage 4 of the inspection apparatus, which performs θ alignment between the pattern 2 formed on the wafer 1 and the stage scan direction. A dark field image of the wafer 1 enables an image of the scattered light to be detected continuously while the stage 4 is being scanned at a constant speed in the X-direction. As a light source, a laser 8 that emits a laser beam of a specific wavelength $\lambda_1$ (e.g., the third harmonic 355 nm of YAG) in a wavelength band from DUV (Deep Ultraviolet) to UV lights is used, and an outputted laser beam of a wavelength $\lambda_1$ ($\lambda_1$ laser beam) reflects on a mirror 201 and on a dichroic mirror 205. Moreover, a $\lambda_2$ laser beam outputted from a laser of a wavelength $\lambda_2$ that emits the $\lambda_2$ laser beam (e.g., the second harmonic 532 nm of YAG) different from that of the laser 8 of a wavelength of $\lambda_1$ is transmitted through the dichroic mirror 205, and propagates on the same optical axis as that of the $\lambda_1$ laser beam. The laser beams of two wavelengths $\lambda_1, \lambda_2$ reflect on a mirror 207, are transmitted through a ½ wave plate 210, and are branched to two optical paths by a half mirror 220 with small wavelength dependency. The $\lambda_1, \lambda_2$ lights that reflected on the half mirror 220 reflect on a mirror 270 equipped with a mirror position control mechanism 260, and are transmitted through a ½ wave plate 280 and a ¼ wave plate 290. These wave plates 280, 290 converts the lights to a predetermined S/P circularly polarized lights to the wafer 1 or lights in intermediate polarization states between them. The lights come incident on a lens 295 and illuminate the wafer 1 in the shape of a strip with its longitudinal side lying in the Y-direction.

On the other hand, the $\lambda_1, \lambda_2$ laser beams that were transmitted through the half mirror 220 are transmitted through a ¼ wave plate 225, reflects on a mirror 230, reflect on a mirror 250 equipped with a mirror position control mechanism 240, and illuminate the wafer 1 through a lens 255 in the shape of a strip with its longitudinal side lying in the Y-direction. The mirror position control mechanisms 240, 260 can control mirrors that are attached to each of them in height and angle, and make it possible to control elevation angles from which the wafer 1 is illuminated, respectively. Although, in this embodiment, simultaneous illumination from two directions of X and Y using the half mirror 220 was described as the embodiment, an embodiment in which only illumination from the X-direction is done by removing the half mirror 220 out of the optical path and also an embodiment in which illumination from the Y-direction is done by disposing a mirror that reflects all instead of the half mirror 220 are conceivable.

Further, in this embodiment, although the illuminations whose azimuths lie in the X- and Y-directions, respectively, is shown, a form in which illumination is made from an azimuth shifted from the Y-axis, for example, by 45 degrees or 20 degrees is conceivable as a modification of this embodiment. In addition, it becomes possible by using a dichroic mirror instead of the half mirror 220 to perform an illumination whose wavelength is different for each illumination azimuth. A reason of changing the illumination elevation angle and the illumination azimuth is to provide a function of setting a condition advantageous to inspection according to the defect and pattern that becomes an inspection object because a scattering distribution is different according to directionality of the defect and pattern, a shape of the defect, and unevenness (e.g., a foreign material taking a shape of a convexity in the Z-direction and a scratch taking a shape of concavity). The scattered light from the defect 3 or the pattern 2 forms a scattered image on the image sensor 100 with the light of a wavelength $\lambda_1$ that is transmitted through a dichroic mirror 32 after through the objective lens 10, the spatial filter 20, and the dichroic mirror 32. A scattered image by the light of a wavelength $\lambda_2$ that reflected on the dichroic mirror 25 is formed on the image sensor 110. The detected image is inputted into an image processing section 300, which compares it with an image of an identical design pattern, for example, an image of an adjacent die, and detects the defect 3. Defect information, such as coordinates, dimensions, and brightness of the detected defect, is sent to a control section 320. Then the inspection apparatus user is enabled to make the apparatus display the defect information, such as a defect map on the wafer, and to make it output defect information data.

Moreover, the control section 320 is also equipped with a function of performing operation instruction of the inspection apparatus, and gives instructions of operations to a mechanism control section 330, which controls operations of the stage 4 and an optical system mechanism control section 340. As a spatial filter that this optical system uses, there are a micro shutter array that utilizes an electro-optic effect of the double refraction element (LiNbO$_3$, PLZT, etc.) and filters in the form of a one-dimensional array and in the form of a two-dimensional array each of which uses a liquid crystal filter and an MEMS (Micro Electro Mechanical Systems), as embodiments. In these devices, since transmission/shielding of the light can be switched by electrical control at high speed, it becomes possible to changeover the filtering pattern to a suitable one according to the pitch and shape of the pattern 2 on the wafer 1 during the inspection. FIG. 3D shows its form. A two-dimensional spatial filter 500 is disposed on the rear side focal plane (an exit pupil plane) or at its conjugate position of the objective lens 10 where the diffracted image is formed. A setting of shielding a pixel 510 of the two-dimensional spatial filter 500 at a position at which the diffracted image is formed is made. By this setting, an aperture ratio of the exit pupil becomes larger than shielding of diffracted images 410, 430 made by a light shielding belt 420 shown in FIG. 3C, and therefore lowering of the resolution of the optical system can be suppressed.

Second Embodiment

Figure 4A:
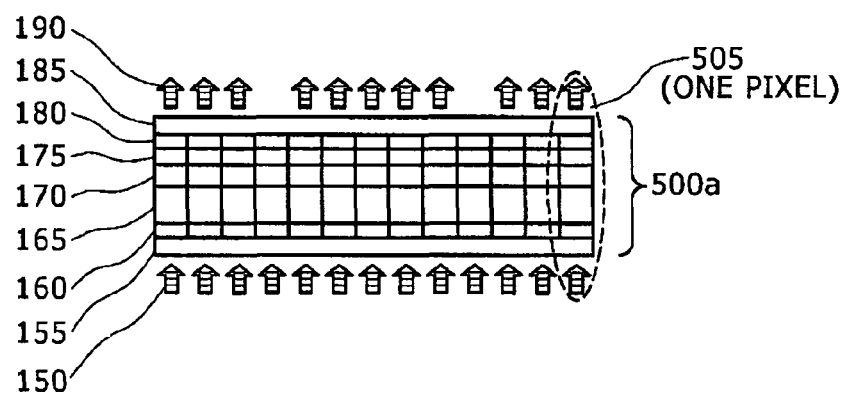
FIG. 4A shows an example in which a liquid crystal filter 500a is used as a spatial filtering device.

FIG. 4A shows an example in which a liquid crystal filter 500*a* is used as a spatial filtering device. Only the linearly polarized light corresponding to a transmission axis of a liquid crystal filter incident light 150 is transmitted through a first polarizing plate 155. In a TFT (Thin Film Transistor) substrate 160, an impressed voltage of an illumination electrode 180 is controlled to change alignment of a liquid crystal 170 that is sealed in between two orienting films 165, 175. This configuration makes it possible to control the transmittance of the filter transmitted light that is transmitted through a second polarizing plate 185 according to the alignment of this liquid crystal 170. This liquid crystal filter 500a is such that pixels are arranged in the form of a two-dimensional array, and the transmittance of the light can be controlled for every pixel 505.

Figure 4B:
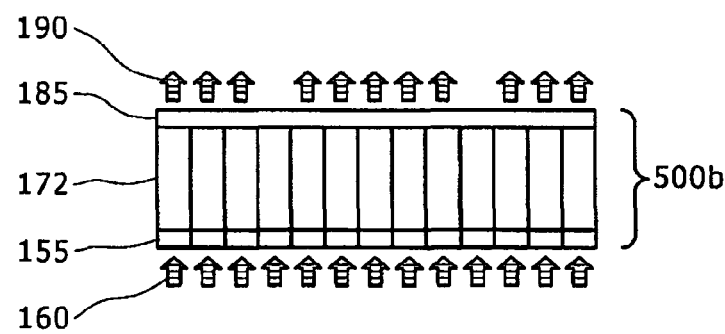
FIG. 4B shows a structure of the two-dimensional spatial filter utilizing an electro-optic effect.

FIG. 4B shows a structure of a two-dimensional spatial filter 500b that utilizes the electro-optic effect. Regarding the incident light 150, its linear polarization component is transmitted through the first polarizing plate 155, and comes incident on a double refraction material 172 that has the electro-optic effect, such as PLZT (abbreviation of (Pb, La)(Zr, Ti)O$_3$) and LiNbO$_3$. This double refraction material 172 is such that pixels are arranged in the form of a one-dimensional or two-dimensional array, which makes it possible to control an oscillating direction of the linearly polarized light having entered according to the impression voltage of the electrode formed for each pixel, and accordingly to change the transmittance of the second polarizing plate 185.

Figure 4C:
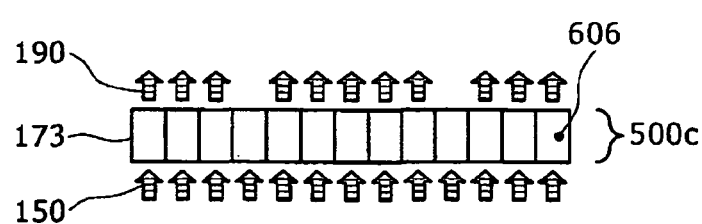
FIG. 4C shows a structure of a two-dimensional spatial filter 500c using a MEMS.
Figure 4D:
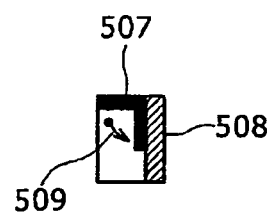
FIG. 4D is a diagram showing a configuration of one pixel of the MEMS in which pixels are arranged in the form of a two dimensional array.

FIG. 4C shows a structure of a two-dimensional spatial filter 500c using the MEMS. The MEMS has pixels that are arranged in the form of a two-dimensional array, and in every pixel 506, a shielding part 507 shown in FIG. 4D and an electrode 508 are formed. Impression of a predetermined voltage to the shielding part 507 and the electrode 508 causes the shielding part 507 to fall on the electrode 508 side by the action of electrostatic capacity, which makes it possible to transmit the incident light. For this reason, it becomes possible, by controlling the impressed voltage to the shielded part 507 and the electrode 508, for open/close states of the shielded part 507 to be switched and for transmission/shielding of the incident light to be controlled on a pixel basis.

Third Embodiment

With the two-dimensional spatial filter shown in FIG. 3D and FIG. 4, the pixel 510 to be shielded is shielded for the lights of two wavelengths $\lambda_1$, $\lambda_2$. However, since positions of the diffracted lights of wavelengths $\lambda_1$, $\lambda_2$ do not coincide with each other, the pixel on which the diffracted image of a wavelength $\lambda_1$ is formed shields only the $\lambda_1$ light, and the pixel on which the diffracted image of a wavelength $\lambda_2$ is formed shields only the $\lambda_2$ light; therefore, a substantial aperture becomes larger.

Figure 5:
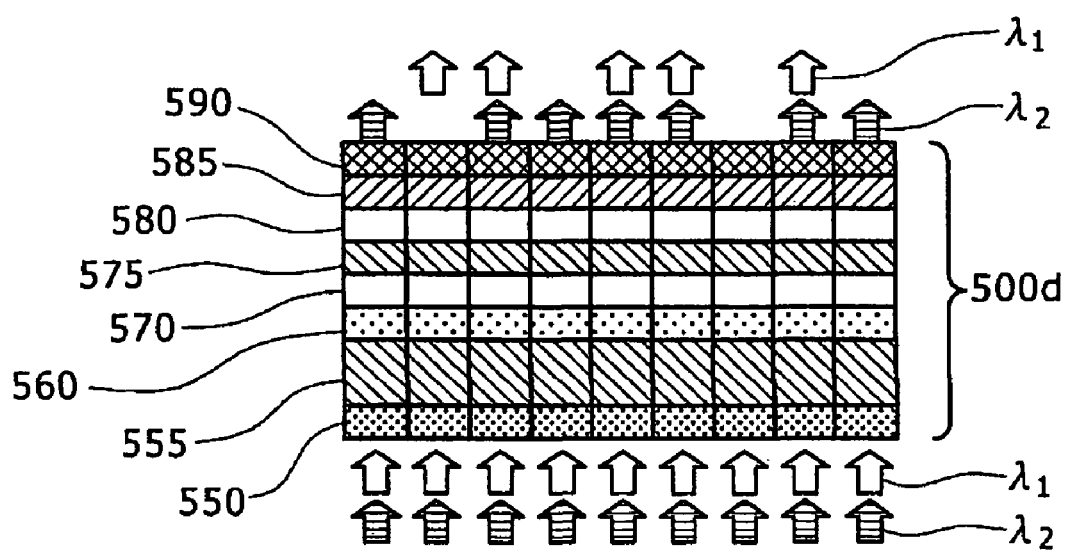
FIG. 5 is a diagram showing an outline configuration of a two-dimensional array liquid crystal tunable filter.

FIG. 5 shows an example in which a two-dimensional array liquid crystal tunable filter 500d that is formed by arranging liquid crystal tunable filters LCTF's (Liquid Crystal Tunable Filter) using a principle of the Lyot filter in the form of a two-dimensional array is used as the spatial filter. When the lights of wavelengths $\lambda_1$, $\lambda_2$ come incident on a first polarizing plate 550, the two lights become the linearly polarized lights, enter the wave plate 555, and are given a phase difference between them. In a TFT (Thin Film Transistor) substrate 560, by making alignment of a liquid crystal 575 sealed in between an orienting film 570 and an orienting film 580 be switched, lights that are transmitted though a transparent electrode 585 and a second polarizing plate 590 are detected. This configuration enables transmission/shielding to be controlled by selecting a wavelength.

Figure 6A:
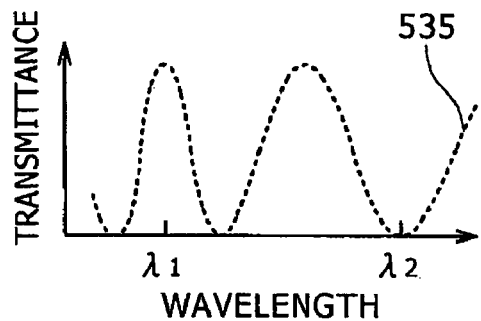
FIG. 6A shows a spectral transmission characteristic under a condition that allows a $\lambda_1$ light to be transmitted.
Figure 6B:
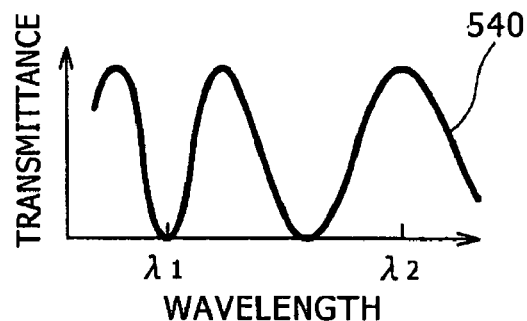
FIG. 6B shows a spectral transmission characteristic under a condition that allows a $\lambda_2$ light to be transmitted.
Figure 6C:
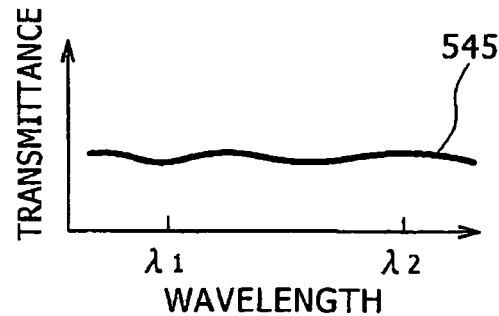
FIG. 6C shows a spectral transmission characteristic under a condition that allows both the $\lambda_1$ light and the $\lambda_2$ light to be transmitted.
Figure 6D:
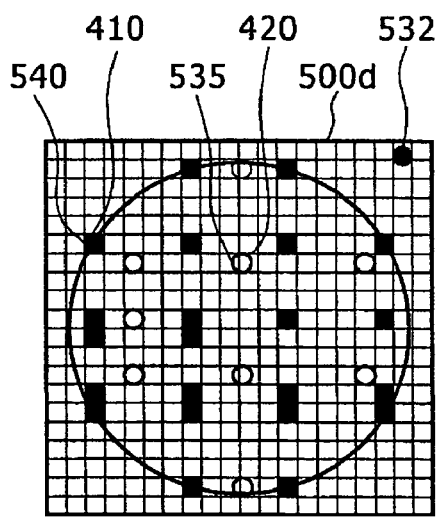
FIG. 6D shows a case where the two-dimensional array liquid crystal tunable filter is used as the spatial filter.

FIG. 6A shows a spectral transmission characteristic using a condition that allows the $\lambda_1$ light to be transmitted. FIG. 6B is a spectral transmittance under a condition that allows the $\lambda_2$ light to be transmitted, and FIG. 6C is the same characteristic under a condition that allows both the $\lambda_1$, $\lambda_2$ lights to be transmitted. FIG. 6D shows a state when the two-dimensional array liquid crystal tunable filter 500d is used as the spatial filter. By adopting an optical condition in which each light is shielded at a pixel corresponding to a position at which the diffracted images 410, 430 of the $\lambda_1$, $\lambda_2$ lights are formed, it becomes possible to shield the $\lambda_1$ light and to allow the $\lambda_2$ light to be transmitted, for example, and accordingly it becomes possible to suppress unnecessary shielding of the aperture.

Fourth Embodiment

Since the spatial filter shown in FIGS. 4A, 4B and FIG. 5 needs the incident light to become a linearly polarized light, a polarizing plate is disposed on the incidence side thereof. The scattered light from the defect that will be an object of detection has a polarization characteristic and its polarization state changes depending on the kind of the defect. For example, there occur phenomena that when the defect is illuminated with the linearly polarized light, the scattered light may become an elliptically polarized light and that the major axis of an ellipse may rotate (optical rotation).

Figure 7:
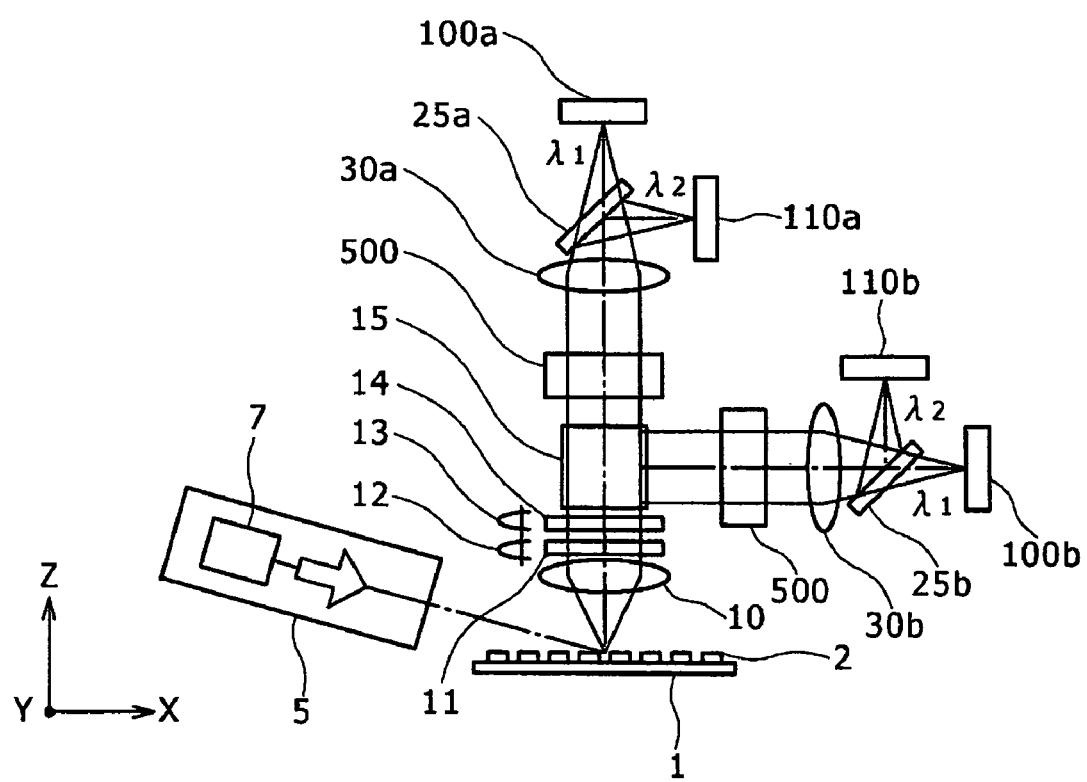
FIG. 7 is a diagram showing the outline of an optical system shown in this fourth embodiment.

For this reason, when only specific polarization is detected, there will be a possibility of overlooking defects because the defect scattered light is shielded. Because of this, there is an optical system for preventing the overlooking even when the spatial filter 500 shown in FIGS. 4A, 4B and FIG. 5 is used. FIG. 7 shows a configuration of it. A polarizing beam splitter 15 is disposed in the detection optical path, aiming to split the light into two pieces of linearly polarized light. The detection system is divided for the two optical paths and the spatial filters 500 are disposed in the respective optical paths. This realizes a configuration capable of detecting the scattered light from various defects without shielding it. Dichroic mirrors 25a, 25b are disposed in the respective optical paths to perform spectral splitting and image sensors 100a, 110a, 100b, and 110b are disposed in the respective optical paths to detect scattered images.

Figure 8A:
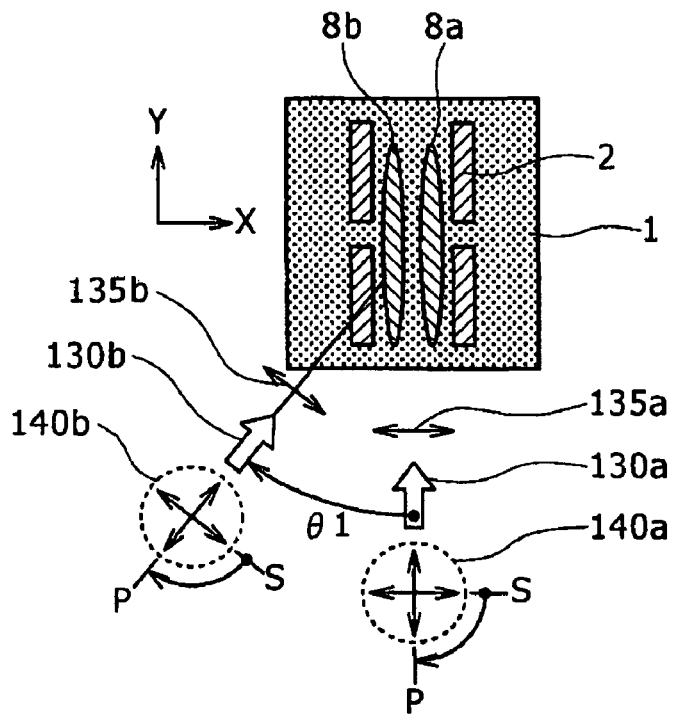
FIG. 8A shows an azimuth of the illumination light relative to the wafer and a definition of polarization of the illumination light.
Figure 8B:
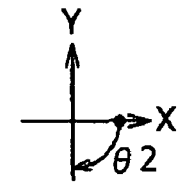
FIG. 8B defines a direction of a transmission axis of an analyzer.
Figure 8C:
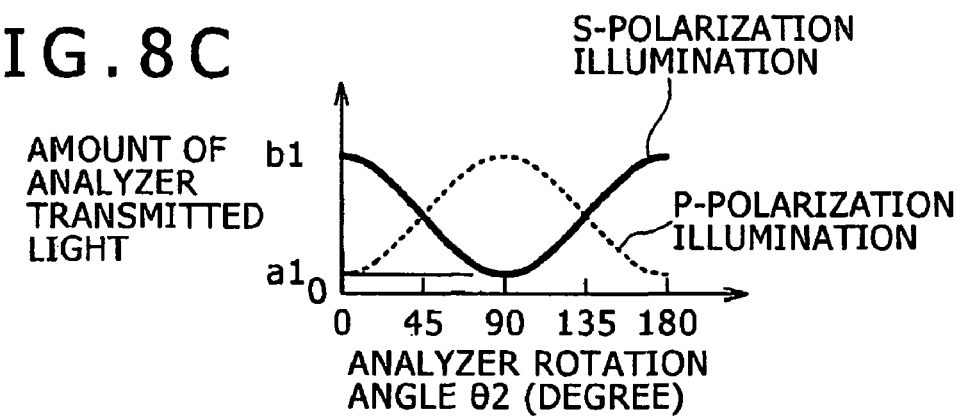
FIG. 8C shows an amount of analyzer transmitted light of pattern scattered light when Y-direction illumination is performed by S-polarization illumination and P-polarization illumination.

Incidentally, a ¼ wave plate 11 attached with a rotation function 12 and a ½ wave plate attached with a rotation function 13 are disposed between the objective lens 10 and the polarizing beam splitter 15. This operation will be explained using FIG. 8. FIG. 8A shows definitions of an orientation of illumination light and polarization of the illumination light to the wafer 1. An illumination light 130a illuminates the wafer 1 from the Y-direction slantingly. An insert 140a shows a cross section of this illumination light, being perpendicular to its optical axis. Taking the S-polarization relative to the wafer 1 as a reference, if the polarization (the oscillating direction of an electric field vector) rotates clockwise by 90 degrees, it will become P-polarization illumination. The oscillating direction of polarization in the case of S-polarization illumination becomes as shown by an insert 135a. On the other hand, when an illumination azimuth rotates by $\theta_1$, the oscillating direction of the S-polarization of an illumination light 130b becomes as shown by an insert 135b. FIG. 8B defines a direction of the transmission axis of an analyzer (a polarizing plate disposed in a detection optical path on which the objective lens 10 captures the scattered light). This diagram is a plan view seen from the image sensor 100a side assuming that the analyzer is set on a transmission side of the polarizing beam splitter shown in FIG. 7. The X-direction being considered as a reference of the analyzer transmission axis, an angle by which the analyzer (in the example of FIG. 7, the polarizing beam splitter 15) is rotated clockwise is designated by $\theta_2$. FIG. 8C shows an amount of analyzer transmitted light of pattern scattered light in the case where the pattern is illuminated by the S-polarization and the P-polarization in the Y-direction illumination. Regarding the scattered light from the pattern 2 that is parallel or perpendicular to the X- and Y-directions, its transmitted light becomes maximum in the S-polarization illumination with an analyzer rotation angle $\theta_2$ set 0 degree, and becomes minimum in the P-polarization illumination with the same analyzer rotation angle. Moreover, the amount of the transmitted light becomes minimum in the S-polarization illumination with the analyzer rotation angle $\theta_2$ set to 90 degrees, and becomes maximum in the P-polarization illumination.

On the other hand, in the case where the illumination light 130b coming from the $\theta_1$ azimuth (in this example, 45 degrees) shown in FIG. 8A is the S-polarization, the amount of the transmitted light becomes maximum when the analyzer rotation angle $\theta_2$ is equal to $\theta_1$ (in this example, 45 degrees). By the P-polarization illumination, the amount of the transmitted light becomes minimum with the same analyzer rotation angle. For this reason, even when the same S-polarization illumination to the wafer 1 is used, if the illumination azimuth is different, an angle at which the amount of the transmitted light of the analyzer becomes maximum or minimum will be different. Brightness variation of the transmitted light of the pattern caused by LER (Line Edge Roughness) of the pattern, a minute difference of a shape thereof, grain on the surface, and film thickness variation of an interlayer insulating film that do not effect criticality for the semiconductor device becomes a sensitivity hindrance factor (noise light) in detecting the defects. These noise lights have the same characteristics as those of FIGS. 8C and 8D. For this reason, when the S-polarization illumination is performed from the Y-direction relative to the wafer 1 in the configuration of FIG. 7, it is possible for the S-polarization reflected on the polarizing beam splitter 15 to minimize the scattered light and the noise lights from the pattern parallel to or perpendicular to the X- and Y-directions (disposition of the analyzer to establish a cross Nicol state). On the other hand, defects have various directions, and regarding polarization of the defect scattered light, S-polarization that reflects on the polarizing beam splitter 15 does not necessarily cause the minimum. For this reason, the reflected light (S-polarization) of the polarizing beam splitter 15 has a small amount of reflected light of noise light, and an amount of reflected light of the defect scattered light increases. Therefore, a scattered image by S-polarization that reflected on the polarizing beam splitter 15 becomes a high S/N image that is advantageous to defect detection. Incidentally, it may occur that the P-polarization being transmitted through the polarizing beam splitter 15 (deposition of the analyzer so as to be in a parallel Nicol state) yields high S/N depending a shape, a kind, and a material of the defect. For this reason, by detecting simultaneously each of images that are analyzed in conditions of the cross Nicol state (reflection) and of the parallel Nicol state and determining the defects, it becomes possible to improve a capture ratio of the defects existing on the wafer 1.

However, when the Y-direction changes to a direction away from the Y-direction by 45 degrees in FIG. 7 and FIG. 8A, the analyzing directions of the cross Nicol state and the parallel Nicol state change, respectively, even with the same S-polarization illumination relative to the wafer 1. For this reason, by disposing a ½ wave plate 14 attached with the rotation function 13 between the objective lens 10 and the polarizing beam splitter 15 and controlling a rotation angle, even when the illumination azimuth changes, the ½ wave plate 14 is rotated so that the parallel/cross Nicol state is established without rotating the polarizing beam splitter.

Figure 8D:
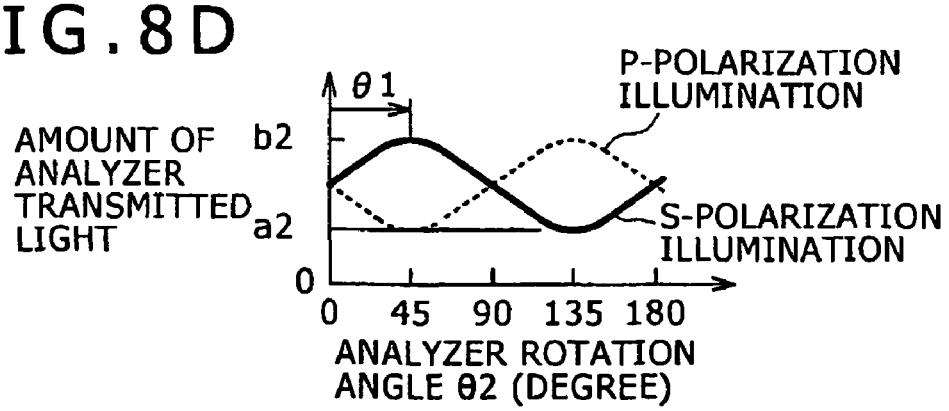
FIG. 8D shows the amount of the analyzer transmitted light of the pattern scattered light when the S-polarization and P-polarization illuminations are performed using the 45-degree azimuth illumination.

Moreover, in the 45-degree azimuth illumination, as shown in FIG. 8D, a ratio ($a_2/b_2$; ellipticity) of a maximum amount of the transmitted light $b_2$ and a minimum amount of transmitted light $a_2$ of the analyzed light becomes larger than a ratio of $b_1$ and $a_1$ shown in FIG. 8C. Therefore, polarization of the pattern scattered light has a comparatively large ellipticity. In such a case, since noise light cannot be suppressed sufficiently in the cross Nicol state, the rotary mechanism 12 is used to control rotation of the ¼ wave plate 11 so that it may converts the elliptically polarized light into a linearly polarized light. This enables the high S/N image to be detected with noise light suppressed, which results in improvement of defect detection sensitivity.

Fifth Embodiment

Figure 9A:
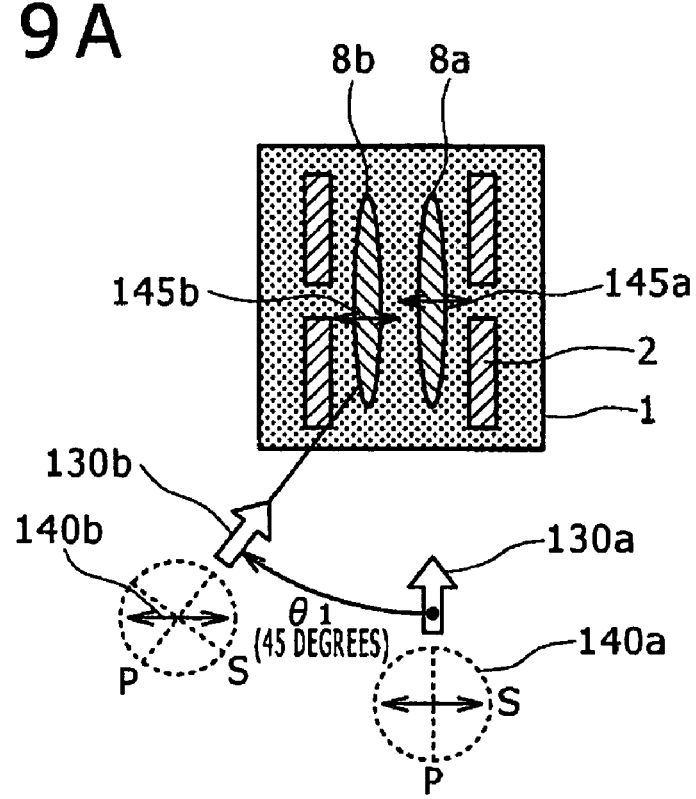
FIG. 9A shows a plan view when the Y-direction illumination with the $\lambda_1$ light and the 45-degree azimuth illumination with the $\lambda_2$ light are performed simultaneously at spatially separated positions on the wafer.

FIG. 9A shows a plan view of an illumination in the case where a Y-direction illumination 130a with the $\lambda_1$ light and the 45-degree azimuth illumination 130b with the $\lambda_2$ light are performed simultaneously at spatially separated positions on the wafer 1. It is configured so that the Y-direction illumination 130a may be the S-polarization illumination relative to the wafer 1, and for the 45-degree azimuth illumination 130b, its projection vector to the wafer 1 may become parallel to the S-polarization of the Y-direction illumination 130. For this reason, the polarization of the 45-degree azimuth illumination becomes intermediate polarization between the S- and P-polarizations relative to the wafer 1. In this case, since the scattered lights of two-direction illumination lights 130a, 130b agree with each other in the oscillating direction of the polarization that establishes the cross Nicol state, it is possible to detect scattered images in the cross Nicol state and in the parallel Nicol state for both the Y-direction and 45-degree azimuth illuminations in the configuration using the polarizing beam splitter 15 shown in FIG. 7.

Figure 9B:
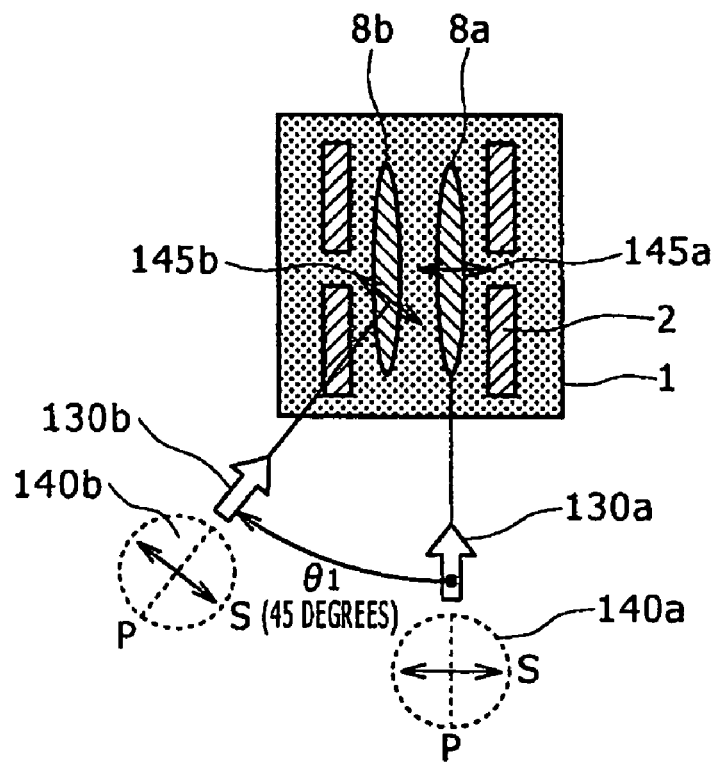
FIG. 9B shows a plan view when the Y-direction illumination with the $\lambda_1$ light and the 45-degree azimuth illumination with the $\lambda_2$ light are performed at spatially separated positions on the wafer by the S-polarization relative to the wafer.
Figure 10:
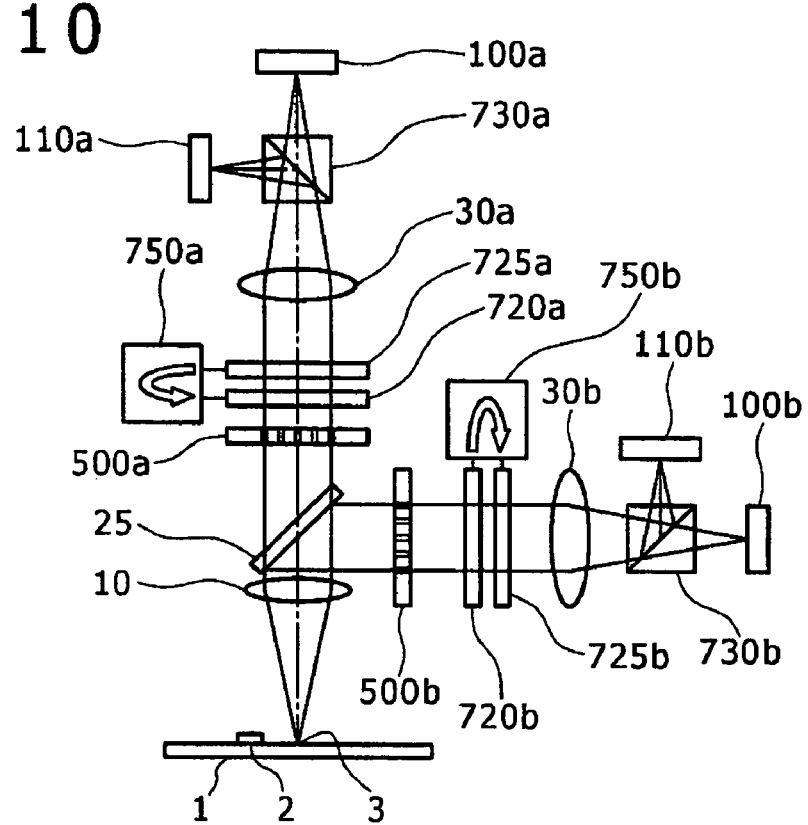
FIG. 10 is a diagram showing an outline configuration of an optical system that will be shown in this fifth embodiment.

On the other hand, as shown in FIG. 9B, it may occur that the defect detection sensitivity can be improved by both the Y-direction illumination 130a of the $\lambda_1$ light and the 45-degree azimuth illumination 130b of the $\lambda_2$ light illuminating the wafer 1 by the S-polarization relative to the wafer 1. Under a simultaneous illumination condition using these two azimuths, such a detection that each illumination azimuth establishes the cross Nicol state cannot be performed with the configuration shown in FIG. 7. For this reason, a configuration of the optical system such that each illumination azimuth establishes the cross Nicol state is used. FIG. 10 shows this optical system. The dichroic mirror 25 allows the $\lambda_1$ light to be transmitted through it and reflects the $\lambda_2$ light. A spatial filter 500a is disposed in the optical path of the $\lambda_1$ light that is transmitted, and is equipped with a ¼ wave plate 720a, a ½ wave plate 725a, and a rotary mechanism 750a that rotates them independently and fixes these positions. Using these rotatable ¼ wave plate 720a and ½ wave plate 725a, a condition whereby the detected scattered light becomes in the cross/parallel Nicol state relative to a polarizing beam splitter 730a or an intermediate analyzing condition that realizes higher S/N is set up. The image sensors 100a, 110a are disposed on respective image planes of the lights that were branched by the polarizing beam splitter 730a by polarization splitting, and two kinds of analyzed dark field images that are formed by the $\lambda_1$ light are detected. Similarly, for the $\lambda_2$ light that reflected on the dichroic mirror 25, a spatial filter 500b, a ¼ wave plate 720b, a ½ wave plate 725b, a rotary mechanism 750b, and a polarizing beam splitter 730b are disposed, and image sensors 100b, 110b are disposed on the respective image planes. With the above techniques, it becomes possible to detect four kinds of images that differ in illumination azimuth, wavelength, and polarization.

Sixth Embodiment

Figure 11:
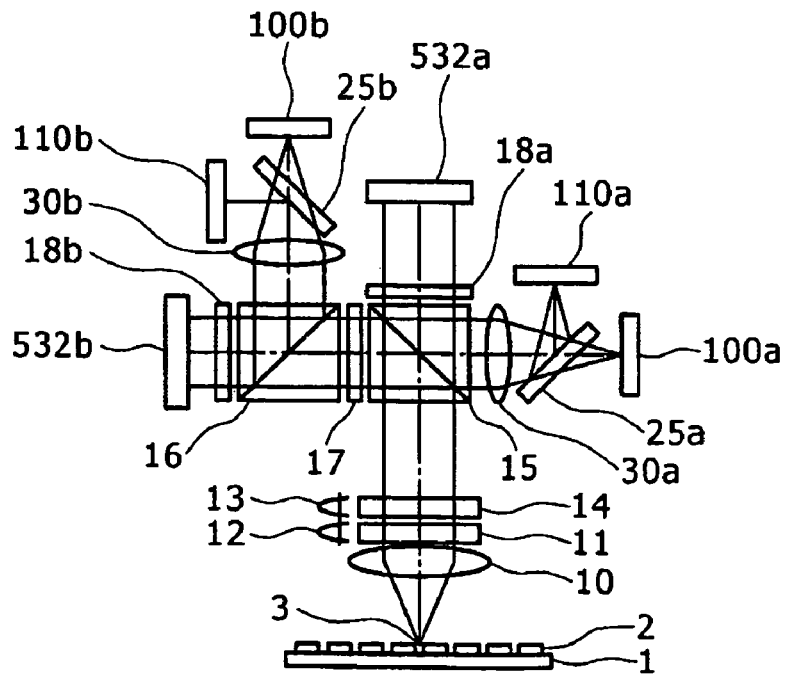
FIG. 11 is a diagram showing an outline configuration of an optical system using a reflection type two-dimensional array spatial filter.

FIG. 11 shows a configuration of the optical system that uses a reflection type spatial light modulator utilizing a DMD (Digital Micromirror Device) in the form of a two-dimensional array as the spatial filter. The scattered light captured by the objective lens 10 is transmitted through the ¼ wave plate 11 attached with the rotary mechanism 12 and the ½ wave plate attached with the rotary mechanism 13 and comes incident on the polarizing beam splitter 15. A P-polarization component that was transmitted through the polarizing beam splitter 15 becomes a circularly polarized light by a ¼ wave plate 18a, and comes incident on a reflection type spatial light modulator 532a that is disposed at the rear side focal point position or its conjugate position of the objective lens 10. The reflection type spatial light modulator 532a is such that an individual mirror plane slants by electric control, and when the diffracted light from a wafer-like pattern is intended to be shielded, the mirror becomes slant to diverge the diffracted light out of the optical path. The mirror plane is set so that light that is intended to be detected may come incident on the mirror perpendicularly with the mirror being not slanted, and the reflected light propagates on the same optical path as the optical path on which the incident light propagated in the reverse direction. The light that is transmitted through the ¼ wave plate 18a again becomes S-polarization relative to the polarizing beam splitter 15, and reflects on it. The reflected light comes incident on an image formation lens 30a and the dichroic mirror 25a. On the image planes of the $\lambda_1$ light having been transmitted through the dichroic mirror 25a and the $\lambda_2$ light having reflected thereon, the image sensors 100a, 110a are disposed, respectively, and the dark field images are detected.

On the other hand, the S-polarization that comes incident on the polarizing beam splitter 15 from the objective lens 10 side and reflects there becomes the P-polarization relative to a second polarizing beam splitter 16 with a ½ wave plate 17, and is transmitted through the polarizing beam splitter 16. This light becomes the circularly polarized light with a ¼ wave plate 18b, and a reflection type spatial light modulator 532b reflects only the diffracted light that is not intended to be detected out of the optical path to effect the shielding. The light becomes the S-polarization again with the ¼ wave plate 18b, and reflects on the polarizing beam splitter 16. Further, on the image planes of the $\lambda_1$ light having been transmitted through the dichroic mirror 25b and of the $\lambda_2$ light having reflected thereon, the image sensors 100b, 110b are disposed, respectively, and the dark field images are detected.

Seventh Embodiment

Figure 12:
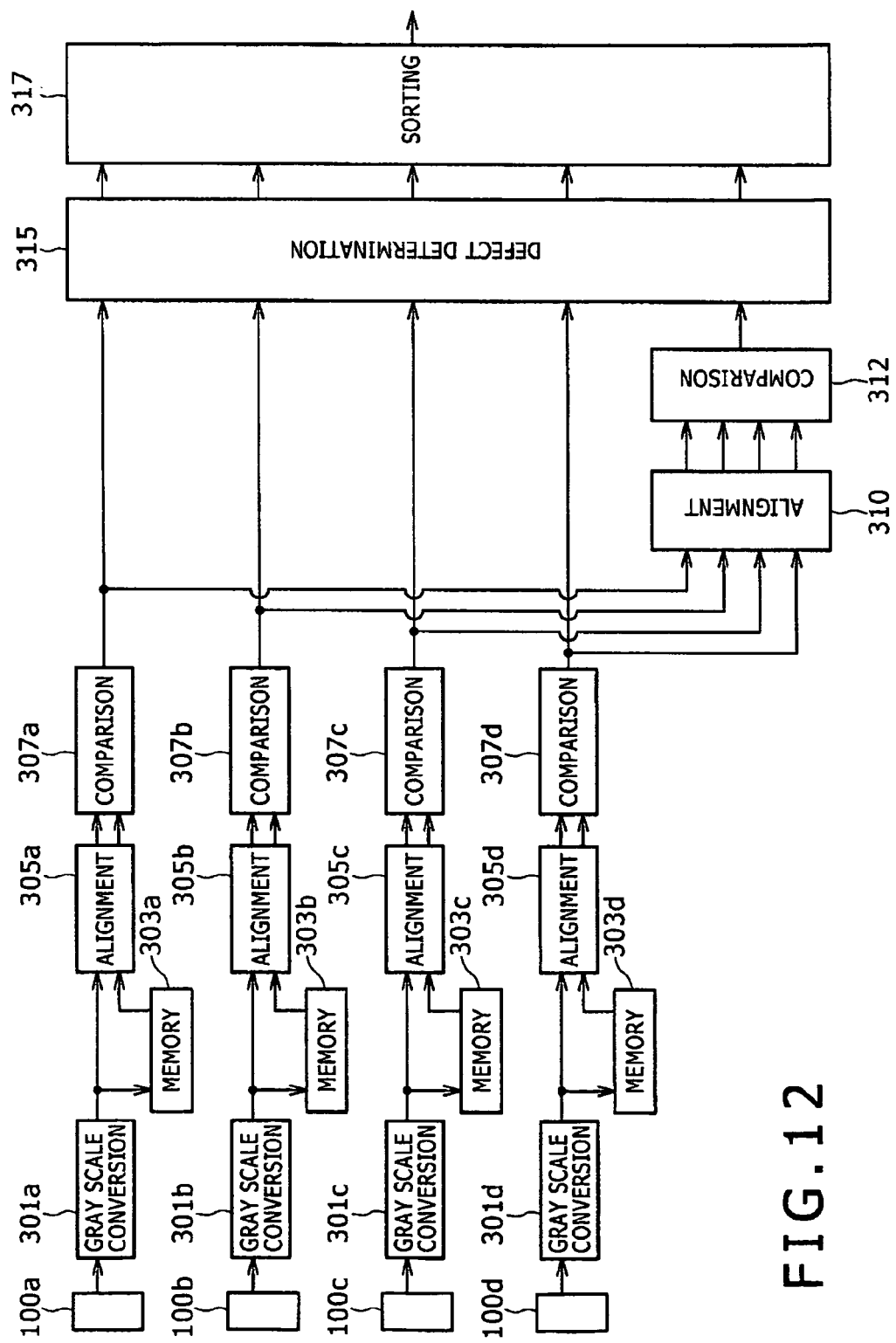
FIG. 12 is a diagram showing an outline configuration of an optical system that will be shown in this seventh embodiment.

FIG. 12 shows a block diagram that illustrates a procedure of processing images detected by these image sensors and determining the defect. The image detected by the image sensor 100a is subjected to conversion of brightness, e.g., γ correction, at a gray-scale conversion section 301a. One portion of the image after the conversion is sent to an alignment section 305a, and other portion is sent to a memory section 303a. In the alignment section 305a, the converted image is stored in the memory section 303a until the converted image has the same pattern as that of the already sent image (e.g., the adjacent die) in terms of design, and is put into alignment with the image sent from the memory section 303a. A comparison section 307a performs comparison processing on a difference image etc. of the two images that were aligned to each other, and computes a feature quantity of the image as a result of the comparison. A defect determination section 315 determines a defect using this feature quantity (e.g., a maximum, an area, etc. of a gray-scale difference). This series of processings are similarly performed for each of the image sensors 100b, 110a, and 110b.

Further, a result obtained by performing comparison for each image is sent to an alignment section 310, which aligns four images different in polarization and wavelength, compares the feature quantities of the images obtained under these different optical conditions, and sends theses feature quantities to the defect determination section 315. The defect determination section 315 determines the defects. As described above, the defect determination section performs the determination using the five kinds of feature quantities. If the image is determined to be the defect by any of the determination results, its feature quantities is sent to a sorting section 317 together with remaining four kinds of feature quantities. This sorting section 317 sorts the kinds of defects (e.g., a foreign material, etching residue, a scratch, etc.) and pseudo defects (brightness unevenness of an oxide film, roughness of the pattern, grain, etc. that have no criticality for a device), and outputs coordinates of defects, a sorting result, feature quantities, etc.

Eighth Embodiment

Figure 13:
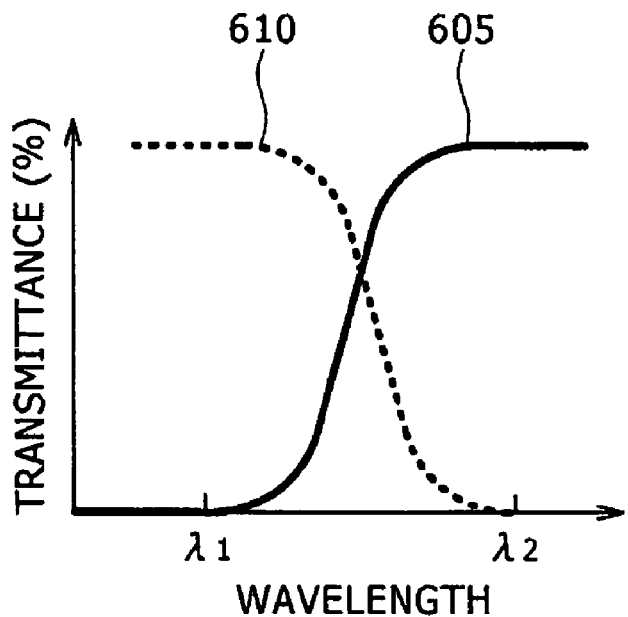
FIG. 13 is a diagram showing an optical characteristic of a spectral transmission filter.
Figure 14:
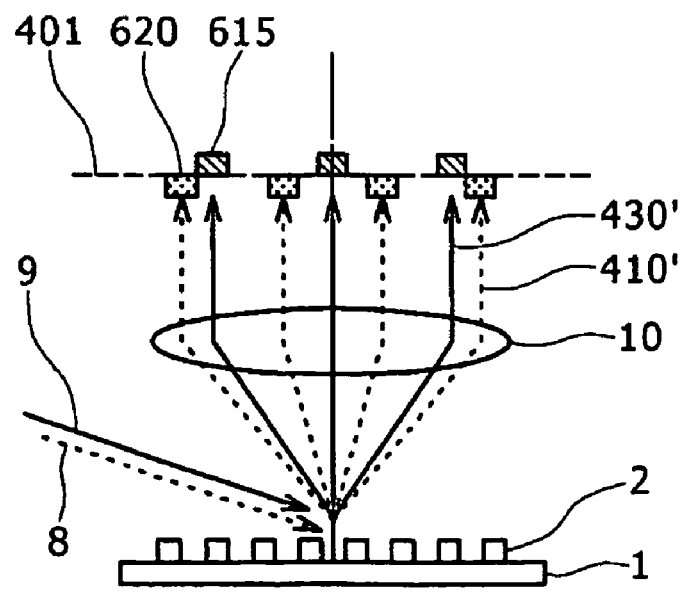
FIG. 14 is a diagram showing disposition of a spectral transmission filter unit.

Next, a technique of spatial filtering that uses wavelength selective filters, such as interference filters and sharp-cut filters, will be explained. FIG. 13 shows two kinds of spectral characteristics. The spectral characteristic of a $\lambda_1$ transmission filter has a characteristic of cutting the $\lambda_2$ light and the spectral characteristic of a $\lambda_2$ transmission filter has a characteristic of cutting the $\lambda_1$ light. FIG. 14 has an example of deposition of the filters having these spectral transmission characteristics. Both the $\lambda_1$ transmission filter 615 and the $\lambda_2$ transmission filter 620 are disposed at the rear side focal point position of the objective lens 10 being adjacent to each other. The both transmission filters are positioned so that the $\lambda_1$ transmission filter 615 may shield the $\lambda_2$ diffracted image 430 and the $\lambda_2$ transmission filter 620 may shield the $\lambda_1$ diffracted image 410.

Figure 15:
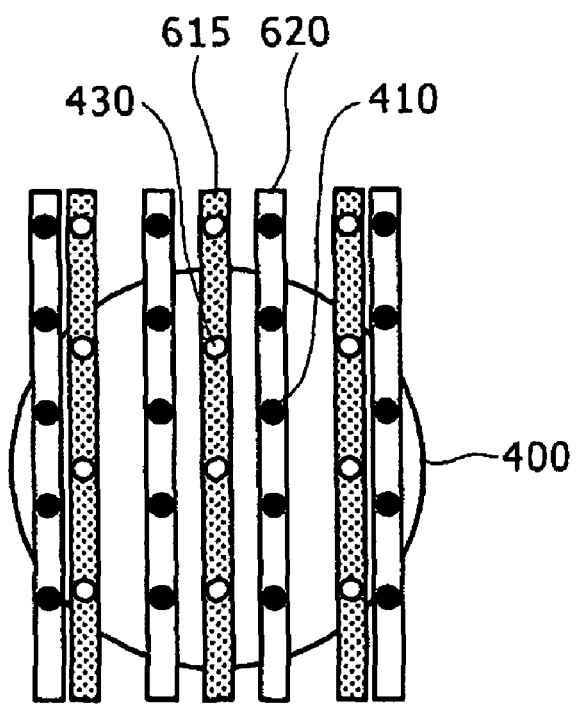
FIG. 15 is a diagram showing an outline configuration of the spectral transmission filter unit.

FIG. 15 shows a schematic diagram of a positional relation of this diffracted light and the transmission filters when seeing the exit pupil of the objective lens projected to a plane. The $\lambda_1$, $\lambda_2$ transmission filters 615, 620 are of a shape of a strip and the plurality of filters are disposed correspondingly to the diffracted lights. These transmission filters 615, 620 have configurations such that positions of the transmission filters are adjustable, respectively, in the case of the $\lambda_1$ transmission filter 615, correspondingly to a pitch of the $\lambda_2$ diffracted image 430 and in the case of the $\lambda_2$ transmission filter 620, correspondingly to a pitch of the $\lambda_1$ diffracted image. However, the optical paths of the light being transmitted through the $\lambda_1$ transmission filter 615 and the light being transmitted through something other than the transmission filter bring about an optical path difference that depends on a refractive index difference of the filter 615 and air and the thickness of the filter. Therefore, the image formed on the image plane deteriorates.

Figure 16:
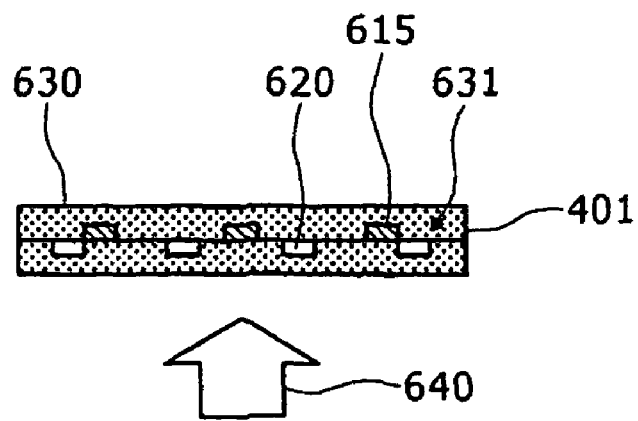
FIG. 16 is a diagram showing an outline configuration of an optical path difference compensation unit.

FIG. 16 shows this countermeasure. In a spectral transmission filter unit 630, the $\lambda_1$ transmission filter 615 and the $\lambda_2$ transmission filter 620 are disposed. An optical path difference correction liquid 631 of the almost same refractive index as the refractive indices of these filters is filled up in the spectral transmission filter unit 630, and reduces the optical path difference of the filter transmitted light and lights other than it.

Ninth Embodiment

Figures 17A, 17B:
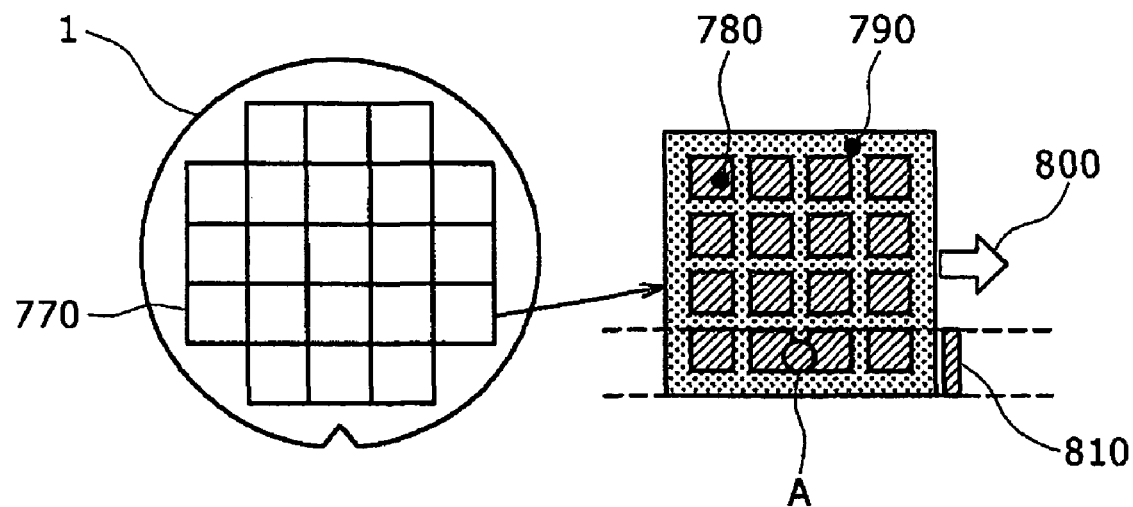
FIG. 17A shows a layout of the wafer and a die.
FIG. 17B is a diagram showing a state in which memory mat parts in the die are formed in the form of a matrix and peripheral circuits are formed between them.
Figure 17C:
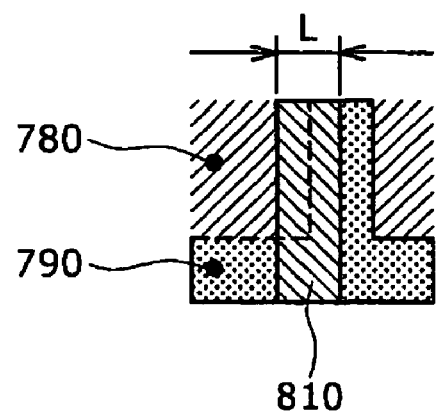
FIG. 17C is a diagram showing a state where an illumination width in a stage scan direction is narrowed.

FIG. 17A shows the wafer 1 and a layout of a die 770. As shown in FIG. 7B, memory mat parts 780 are formed in a matrix manner in the die 770, and a peripheral circuit part 790 is formed between them. A wafer scanning direction 800 at the time of the inspection is assumed a right-hand side, and a field of view at this time is designated as 810. At this time, paying attention to part A of the memory mat edge, since the spatial filtering is performed at the rear side focal point position, diffracted images of the memory mat part 780 and the peripheral circuit part 790 in the field of view are detected as being overlapped. In this case, when the spatial filter is set so that the diffracted light of the memory mat part 780 may be shielded, the diffracted light from the peripheral circuit part 810 whose pattern pitch is different from that the memory mat part 780 will not be shielded, and defect detection performance of the peripheral circuit part 810 will lower. As a countermeasure against this, there is a form in which an illumination width L in the stage scan direction shown in FIG. 17C is made narrower. Expressing the stage scan speed by V mm/s and a switching response frequency of a light shielding part of the spatial filter by R Hz, the illumination width L in the stage scanning direction is set to V/R or less. For example, when V: 1000 mm/s and R: 100 kHz (e.g., the electro-optic effect of $LiNbO_3$) are set, the illumination width L becomes 10 mm. If the illumination width is narrowed smaller than this width 10 mm, the filtering that corresponds to each of the memory mat part 780 and the peripheral circuit part 790 at a boundary part of the both can not be done because of a switching speed of the spatial filter.

Moreover, even if the illumination is performed with the illumination width L narrowed further, there will be no problem in terms of the spatial filtering. However, since the intensity of illumination on the wafer 1 will become higher, it will pose a problem of damages on the wafer 1. For this reason, illumination widths ranging from 10 mm to a minimum line width that provides an illumination intensity giving no damage are suitable illumination widths L. By this, it becomes possible to lower a ratio by which the memory mat part 780 and the peripheral circuit part 790 overlap each other in a width direction in the field of view of detection and to detect the scattered image to which two kinds of the diffracted light are shielded, respectively, by switching a spatial filter condition by which the diffracted light of the memory mat part is shielded even at an edge of the memory mat part a spatial filter condition by which the diffracted light from the peripheral circuit part is shielded even at an edge of the peripheral circuit part. The above enables the wafer to be inspected with high sensitivity even on the boundary between the memory mat part 780 and the peripheral circuit part 790.

Tenth Embodiment

Figure 18:
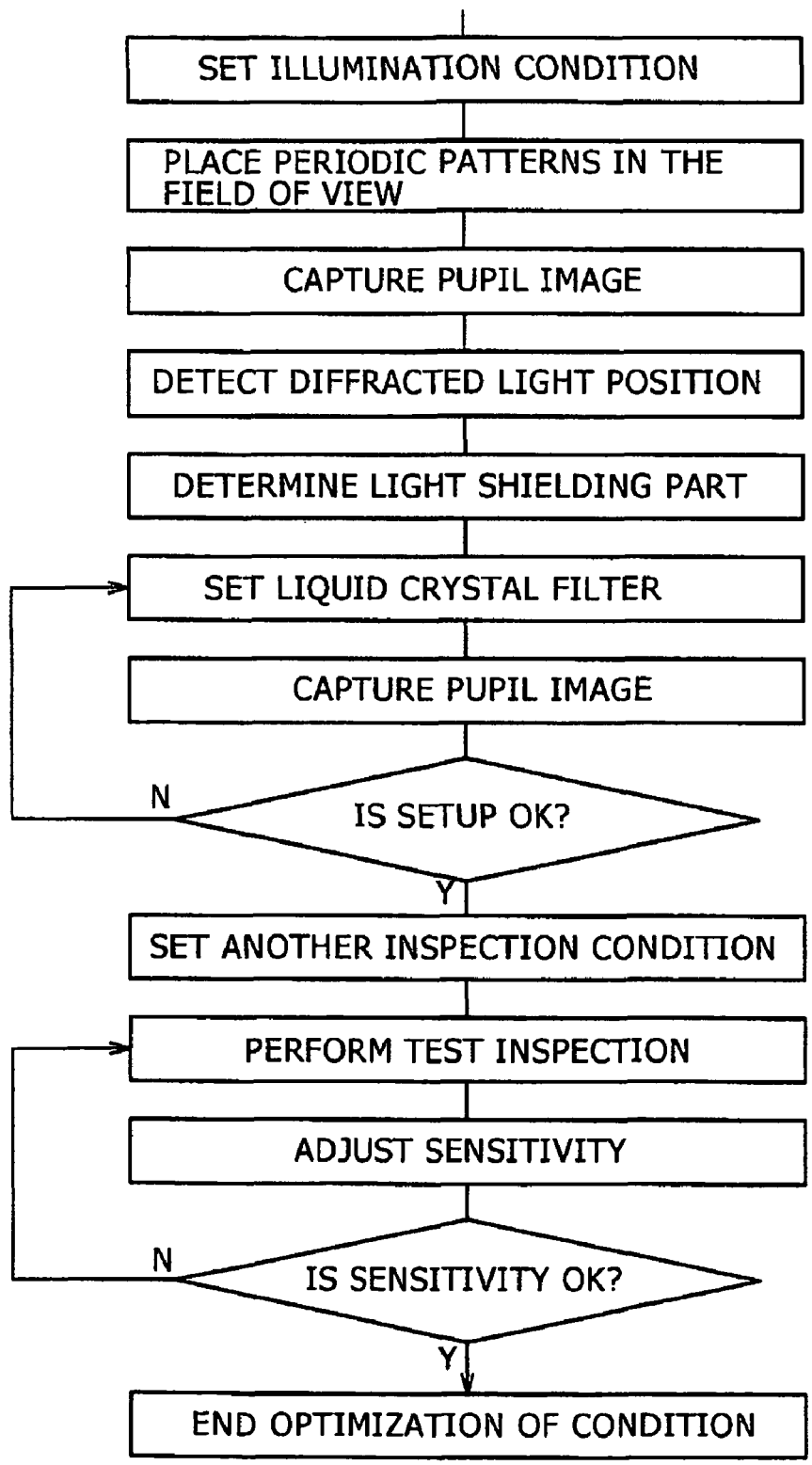
FIG. 18 is a flowchart showing a procedure of optimization of condition.

FIG. 18 shows a technique of optimization of condition by which a condition of the spatial filter is determined. The apparatus places the pattern that is intended to shield the diffracted image in the field of view, takes in a pupil image, detects a position of the diffracted light from the taken-in image, and determines the light shielding part. A condition whereby a pixel of the spatial filter corresponding to the position at which the determination is made is shielded is set up. The pupil image is captured again, and a quality determination of the setup state as to whether there is no leak of the diffracted light is performed. If it is determined not good, the flow returns to the setting of the liquid crystal filter. If it is determined good, another inspection condition is set up, a test inspection and sensitivity adjustment are performed, and the optimization of condition is ended.

Incidentally, in the case where a plurality of pattern pitches exist in the same wafer and shielding conditions of the spatial filter are intended to be set up for respective pitches, the spatial filter is set up for the each pattern pitch. In this case, the setup conditions of the spatial filter is switched in an instance, i.e., within responsibility of 10 ms or less, based on coordinates of the wafer 1 in an actual inspection. Moreover, although being omitted in FIG. 14, the setup of the spatial filter needs to be performed for every wavelength. Although various combinations are conceivable about the configurations, the functions, and the contents of image processing that were shown in the above embodiments, it is evident that those combinations are within the scope of the present invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method that detects defects of a specimen, comprising the steps of:
    scanning a stage that carries a specimen with a circuit pattern formed on it in a horizontal plane;
    illuminating the specimen surface with a plurality of illumination lights each having a different wavelength while keeping a predetermined angle to the normal of the specimen surface;
    capturing scattered light radiated from the specimen surface that is illuminated by the illumination lights with an objective lens;
    shielding a part of the scattered light that was captured by a spatial filtering device in the form of an array;
    branching the scattered light that was not shielded by the spatial filtering device into at least one or more optical paths by spectral splitting or polarization splitting;
    detecting images on image planes on respective optical paths that are branched; and
    determining a defect candidate on the specimen by performing comparison processing on each of the detected images,
    wherein the spatial filtering device comprises a plurality of optical shutters, each of the plurality of optical shutter using a MEMS and the spatial filtering device has a structure in which the optical shutters are arranged in the form of a two-dimensional array that can electrically control transmitted light of the device;
    wherein: in the comparison processing, first defect determination is performed using a plurality of images that differ from one another in at least one condition of a wavelength condition and a polarization condition;
    when the plurality of images are determined as defect candidates in the first defect determination, a result of the first defect determination and the images that were subjected to the defect determination are stored;
    with respect to the images that were not determined as the defect candidates, images in the identical spaces as those of the defect candidates are stored; and second defect determination or defect sorting is performed by comparing feature quantities of the images that were stored and are under the different condition in the identical spaces.

2. The method that detects defects of a specimen according to claim 1,
wherein: the illumination lights have two wavelengths; and
the spatial filtering device is a device with a spectral characteristic of electrically shielding either one of the two wavelengths.

3. The method that detects defects of a specimen according to claim 1,
wherein expressing a scan speed of the stage by V (mm/s) and a switching response frequency of a light shielding part of the spatial filtering device by R (1/sec), a width of the illumination by the illumination light is less than or equal to V/R.

4. A defect inspection method that detects defects of a specimen, comprising the steps of:
scanning a stage that carries a specimen with a circuit pattern formed on it in a horizontal plane;
illuminating the specimen surface using a first illumination light having a first wavelength and a second illumination light having a wavelength different from that of the first illumination light while keeping a predetermined angle to the normal of the specimen surface;
detecting scattered light that is radiated from the specimen surface as being illuminated by the first and second illumination lights;
effecting first branching of the detected scattered light by either one of a wavelength condition or a polarization condition;
shielding a part of the scattered light by disposing spatial filtering devices each in the form of an array at the respective optical paths that were branched by the first branching;
branching the light that was not shielded by the spatial filtering device under a second branching condition different from the first branching condition;
detecting the images on image planes on the respective optical paths that were branched; and
determining defect candidates on the specimen by performing comparison processing on the respective images,
wherein the spatial filtering device comprises a plurality of optical shutters, each of the plurality of optical shutter using a MEMS and the spatial filtering device has a structure in which the optical shutters are arranged in the form of a two-dimensional array that can electrically control transmitted light of the device;
wherein: in the comparison processing, first defect determination is performed using a plurality of images that differ from one another in at least one condition of a wavelength condition and a polarization condition;
when the plurality of images are determined as defect candidates in the first defect determination, a result of the first defect determination and the images that were subjected to the defect determination are stored;
with respect to the images that were not determined as the defect candidates, images in the identical spaces as those of the defect candidates are stored; and
second defect determination or defect sorting is performed by comparing feature quantities of the images that were stored and are with the different conditions in the identical spaces.

5. The method that detects defects of a specimen according to claim 4,
wherein the spatial filtering device is a device that electrically controls transmission and shielding using double refraction elements.

6. The method that detects defects of a specimen according to claim 4,
wherein the illumination lights have two wavelengths, and the spatial filtering device is a device that has a spectral characteristic such that either one of the lights of the two wavelengths is electrically shielded.

7. The method that detects defects of a specimen according to claim 4,
wherein expressing a scan speed of the stage by V (mm/s) and a switching response frequency of a light shielding part of the spatial filtering device by R (1/sec), the width of the illumination by the illumination light is less than or equal to V/R.

8. An apparatus that detects defects of a specimen, comprising:
a scanning section that scans a stage that carries a specimen with a circuit pattern formed on it in a horizontal plane;
illumination means that illuminates lights of two wavelengths or more on a surface of the specimen;
an objective lens that captures scattered light that is radiated from the specimen surface illuminated by the illumination light;
a spatial filtering device that shields a part of the scattered light that was captured and in which elements are arranged one-dimensionally or two-dimensionally;
branching that branches the scattered light that was not shielded to one or more optical paths by spectral splitting or polarization splitting;
image sensors provided on image planes of the respective optical paths that were branched;
an image processing section that performs comparison processing of digital images detected by the image sensors;
a storage section that stores information of the defect detected by the image processing section; and
wherein the spatial filtering device comprises a plurality of optical shutters, each of the plurality of optical shutter using a MEMS and the spatial filtering device has a structure in which the optical shutters are arranged in the form of a two-dimensional array that can electrically control transmitted light of the device;
wherein the image processing section is further equipped with the following configuration:
a first feature computing section that finds a feature quantity of an image as a defect candidate by comparing images of the identical circuit pattern in terms of design under the identical optical condition for a plurality of images that differ from one another in at least one optical condition of a wavelength condition and a polarization condition;
a second feature computing section that finds a feature quantity as a defect candidate by comparing images of the one or more different conditions at the same coordinates as those of the above-mentioned image; and
a defect determination/sorting section that determines a defect using feature quantities computed in the first and second feature computing sections and sorts the determined defect.

9. The apparatus that detects defects of a specimen according to claim 8,
wherein the light source that illuminates the specimen is a lamp, or a plurality of lasers, or a laser that emits laser beams of a plurality of wavelengths.

10. An apparatus that detects defects of a specimen comprising:

a scanning section that scans a stage that carries a specimen with a circuit pattern formed on it in a horizontal plane;

first illumination means that has a first wavelength and illuminates a specimen surface while keeping a predetermined angle to the normal of the surface of the specimen;

a second illumination means that has a wavelength different from the first wavelength and illuminates the specimen surface;

an objective lens that captures scattered light from the specimen surface illuminated by the first and second illumination means;

first branching means that branches the captured scattered light under either one of a wavelength condition or a polarization condition;

spatial filtering devices each of which has elements arranged one-dimensionally or two-dimensionally and that are disposed in the respective optical paths branched by the first branching means;

second branching means that shields a pad of the scattered light having been captured and performs branching under a condition different from that of the first branching means;

image sensors provided on image planes of the respective optical paths that are branched by the first and second branching means;

an image processing section that performs comparison processing of digital images detected by the image sensors; and a storage section that stores information of the defect detected by the image processing, wherein each spatial filtering device comprises a plurality of optical shutters, each of the plurality of optical shutter using a MEMS and the spatial filtering device has a structure in which the optical shutters are arranged in the form of a two-dimensional array that can electrically control transmitted light of the device;

wherein the image processing section further has a following configuration:

a first feature computing section that finds a feature quantity of an image as a defect candidate by comparing images of the identical circuit pattern in terms of design captured under the identical optical condition for a plurality of images that differ from one another in at least one optical condition of a wavelength condition and a polarization condition;

a second feature computing section that finds the feature quantity of an image at the same coordinates as those of the above-mentioned image, as a defect candidate, by comparing the images of the plurality of different conditions; and a defect determination/sorting section that determines a defect using feature quantities computed in the first and second feature computing sections and sorts the determined defect.

11. The apparatus that detects defects of a specimen according to claim 10, wherein the light source that illuminates the specimen is a lamp, or a plurality of lasers, or a laser that emits laser beams of a plurality of wavelengths.

12. The apparatus that detects defects of a specimen according to claim 10, wherein the second illumination means is different from the first illumination means in illumination azimuth, and is equipped with a retardation plate between the objective lens and the branching means based on polarization splitting.

* * * * *